US00PP19795P3

(12) United States Plant Patent
Anderson

(10) Patent No.: US PP19,795 P3
(45) Date of Patent: Mar. 3, 2009

(54) *CHRYSANTHEMUM* PLANT NAMED '01-127-1'

(50) Latin Name: *Chrysanthemum×hybrida*
Varietal Denomination: 01-127-1

(75) Inventor: Neil O. Anderson, St. Paul, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 0 days.

(21) Appl. No.: 11/803,967

(22) Filed: Jun. 18, 2007

(65) Prior Publication Data

US 2007/0271650 P1 Nov. 22, 2007

Related U.S. Application Data

(60) Provisional application No. 60/801,190, filed on May 17, 2006.

(51) Int. Cl.
*A01H 5/00* (2006.01)

(52) U.S. Cl. ..... Plt./286

(58) Field of Classification Search ..... Plt./286
See application file for complete search history.

*Primary Examiner*—Annette H Para
*Assistant Examiner*—S. B McCormick Ewoldt
(74) *Attorney, Agent, or Firm*—Penny J. Aguirre

(57) ABSTRACT

A new cultivar of *chrysanthemum,* '01-127-1', characterized by it's early blooming habit with frost tolerant daisy-type inflorescences with light lavender ray florets and gold disk florets, its vigorous shrub-like growth habit after two years of growth, its tight cushion plant form attained without pinching, and its good garden performance and winter hardiness.

2 Drawing Sheets

STATEMENT REGARDING FEDERALLY SPONSORED RESEARCH

This invention was made with government support under MIN-21-50 awarded by the U.S. Dept. of Agriculture. The government has certain rights in the invention.

Botanical classification: *Chrysanthemum×hybrida.*

Variety denomination: '01-127-1'.

BACKGROUND OF THE INVENTION

The present invention relates to a new and distinct cultivar of garden *chrysanthemum* plant, botanically known as *Chrysanthemum×hybrida* '01-127-1' and will be referred to hereinafter by its cultivar name, '01-127-1'. The new cultivar is commercially known as a garden-type *chrysanthemum.*

'01-127-1' was derived from an on going controlled breeding program that focuses on obtaining new cultivars of garden *chrysanthemums* in a range of flower colors that exhibit superior winter hardiness for northern climates, a large shrub-like habit in successive growth years that, and a tight cushion plant habit without the need for pruning or pinching. The breeding originally commenced with crosses utilizing *Dendranthema weyrichii* 'Pink Bomb' (not patented) and various cultivars of *Dendranthema× grandiflora.*

The new cultivar, '01-127-1' was created with a series of crosses and selections made over a period of tens years between 1990 and 2001 utilizing proprietary selections. '01-127-1' ultimately originated from a cross-pollination made in 2000 of proprietary seedling designated as '92-11-1' (not patented) as the female parent and the proprietary seedling designated as '00-48-30' (not patented) as the male parent. The new *chrysanthemum* was selected as a single plant within the progeny of the stated cross in 2001 by the inventor in St. Paul, Minn. '01-127-1' was selected as unique for its early-blooming, daisy-type inflorescences with light lavender ray florets and gold disk florets combined with the characteristics that fit the objectives of the breeding program.

Asexual reproduction of the new cultivar was first accomplished via stem cuttings in St. Paul, Minn. in 2001. The characteristics of this cultivar have been determined to be stable and are reproduced true to type in successive generations.

SUMMARY OF THE INVENTION

The following traits have been repeatedly observed and are determined to be the characteristics of the new cultivar of *chrysanthemum.* These attributes in combination distinguish '01-127-1' as unique from and all other varieties of *chrysanthemum* known to the inventor.

1. '01-127-1' is early flowering with daisy-type inflorescences with light lavender ray florets and gold disk florets.
2. '01-127-1' attains a large shrub-like habit in the second and successive years of growth attaining about 27 cm in height the first year and about 62 cm in height in the second year and about 75 cm in width the first year and 133 cm in width in the second year.
3. '01-127-1' forms a tight cushion plant form without the need for pinching or pruning.
4. '01-127-1' exhibits extreme hybrid vigor.
5. '01-127-1' exhibits a massive floral display in its second and subsequent years after planting.
6. '01-127-1' is a winter hardy shrub *chrysanthemum* with hardiness to U.S.D.A. Zone 3.
7. The flowers of '01-127-1' are frost tolerant.

In comparison to the parent plants; the female parent, '92-11-1', differs from '01-127-1' in having bronze colored flowers, quadriplex daisy type flowers, and blooming later (mid season) and the male parent, '00-48-30', differs from '01-127-1' in having bronze colored semi-double flowers.

'Cecilia' (not patented) is the closest comparison plant to '01-127-1'. 'Cecilia' is a 7 week variety (mid season), whereas '01-127-1' is a 6 week response group (early season), which means it will flower about 1 week earlier than 'Cecilia'. 'Cecilia' is similar to '01-127-1' in flower color, however '01-127-1' has more petalage than 'Cecilia'. '01-127-1' also has the same plant growth habit as 'Cecilia' (cushion or ball-shaped) but differs by being more winter hardy than 'Cecilia' and growing to a much larger sized plant (both in height and width) in the 2nd and successive years of growth. The frost tolerance provides an extended flowering season when compared with 'Cecilia'.

BRIEF DESCRIPTION OF THE DRAWINGS

The accompanying colored photographs illustrate the overall appearance and distinct characteristics of the new *chrysanthemum*. The photographs were taken of plants grown for one or two years under field conditions in Waseca, Minn.

Figure 1:
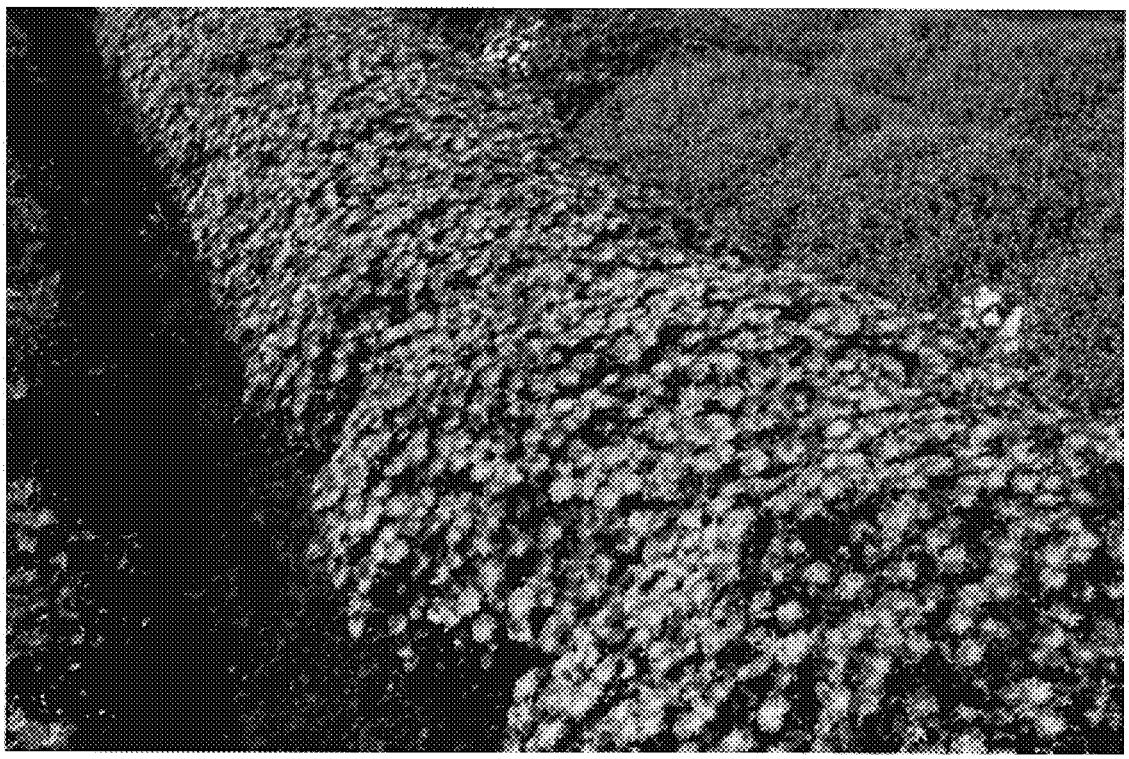
FIG. 1 is a photograph of a row of '01-127-1' after two years of growth.
Figure 2:
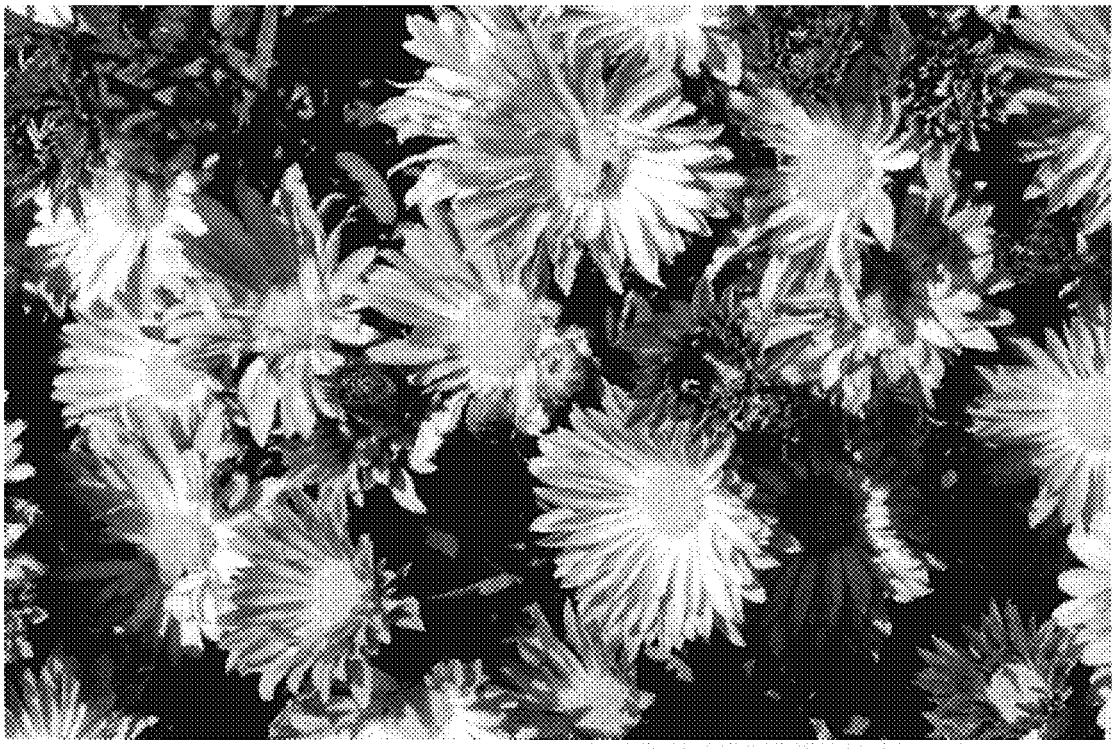

The photograph in FIG. 2 provides a close-up view of the flowers of '01-127-1'.

Figure 3:
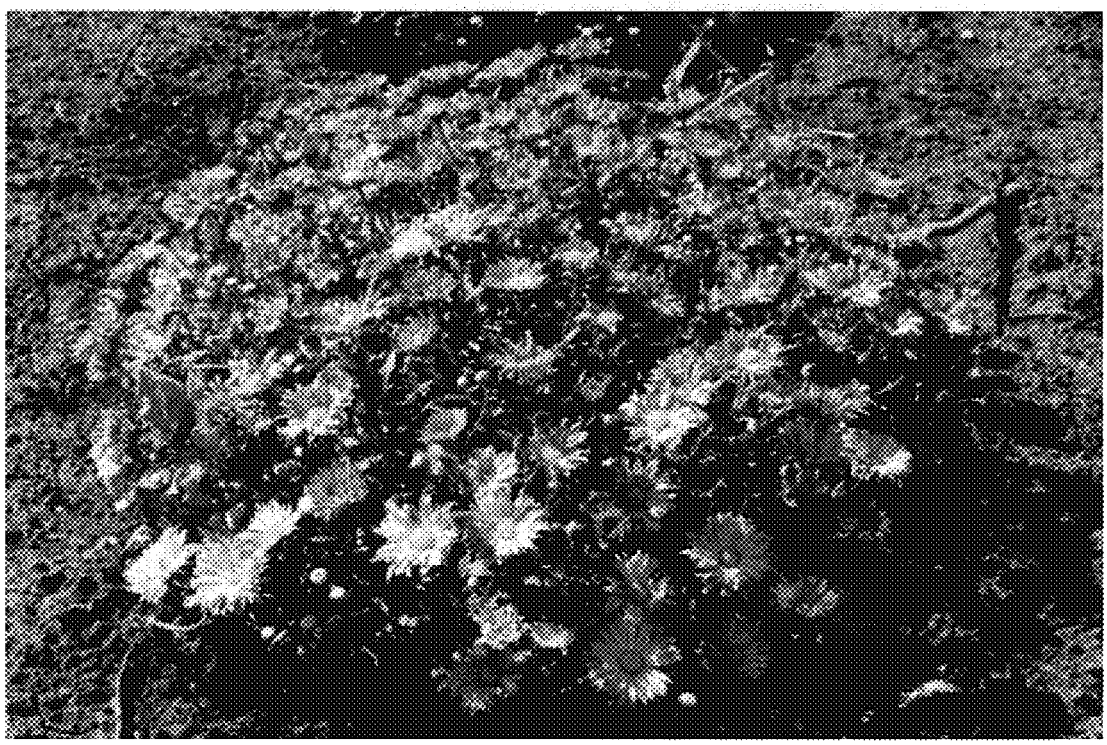

FIG. 3 is a photograph of a single plant of '01-127-1' after one year of growth.

The colors in the photographs are as close as possible with the photographic and printing technology utilized. The color values cited in the detailed botanical description accurately describe the colors of the new *chrysanthemum*.

DETAILED BOTANICAL DESCRIPTION

The following is a detailed description of the new cultivar as grown outdoors under natural lighting in a trial bed in Waseca, Minn. and observed over a period of two years. The detailed botanical data was collected from one and two year-old plants between 1:00 and 5:00 p.m. on Sep. 27, 2005. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General description:

*Blooming season.*—Early blooming, approximately from week 33 in Grand Rapids, Minn. (USDA Z3) and continues through week 40 until a killing freeze. In Waseca, Minn. (USDA Z4), '01-127-1' flowers as early as week 30 and extends through approx. week 40.

*Plant habit.*—Herbaceous perennial, mounded habit, first year growth habit is semi-prostrate, attains a large shrub-like habit in the second and subsequent years with a tight cushion plant form.

*Height and spread.*—Reaches about 27 cm in height and 75 cm in width the first year and about 62 cm in height and 133 cm in width in the second and subsequent years.

*Hardiness.*—U.S.D.A. Zones 3.

*Diseases resistance.*—No susceptibility or resistance to diseases common to *Chrysanthemum* has been observed.

*Root description.*—Fibrous.

Growth and propagation:

*Propagation.*—Stem cuttings.

*Time to root initiation.*—About 1 week.

*Crop maintenance.*—No pinching or pruning is required to achieve the cushion plant habit and abundant bloom.

*Growth rate.*—Vigorous.

Stem description:

*Stem color.*—First year growth 144A, second year growth 144B to 144C.

*Lateral branch length.*—Average of 24 cm.

*Lateral branch diameter.*—2.5 mm.

*Quantity of lateral branches.*—160 per plant, average of 3.7 lateral branches produced per stem when apical meristem is removed (pinched).

*Internode length.*—1.3 cm.

Foliage description:

*Leaf division.*—Simple.

*Leaf shape.*—Blade is ovate to obovate with narrow region extending towards base.

*Leaf base.*—Cuneate.

*Leaf apex.*—Mucronate.

*Leaf margin.*—Incised (mulberry-like incisions) to 1 cm deep.

*Leaf venation.*—Upper surface 147C, lower surface 138C.

*Leaf attachment.*—Sessile.

*Leaf arrangement.*—Alternate.

*Leaf number.*—Average of 18.25 per lateral branch.

*Leaf surface.*—Glabrous on upper surface, slightly pubescent on lower surface.

*Leaf color.*—Young foliage; upper surface 137A, lower surface 137C, mature foliage; upper surface 137B, lower surfaces 138B.

*Leaf size (fully expanded).*—Average of 5.5 cm in length and 2.9 cm in width.

*Fragrance of foliage.*—Fragrant if bruised.

Flower description:

General description:

*Inflorescence type.*—Composite.

*Flowering response.*—6 weeks of short days.

*Lastingness of inflorescence.*—Temperature dependent, under normal field conditions during the fall, flowers typically last about 4–7 weeks.

*Fragrance.*—None.

*Quantity of inflorescences.*—About 6,080 flowers per plant in second year.

*Inflorescence buds.*—About 7.4 mm in depth and 5 mm in diameter, flattened globose in shape, color 138C with stripes on phyllaries 138A.

*Inflorescence size.*—About 1.4 cm in depth and 6.35 cm in diameter, diameter of disk 1.3 cm.

*Peduncle.*—Strong, held at an angle of 55° to stem, texture is hirsute, first peduncle is an average of 11 cm in length and fourth peduncle is an average of about 15.25 in length, color is 144A with hairy coating of 144D.

*Involucral bracts (phyllaries).*—Crenulate in appearance, 137B in color, about 2 to 4 mm in length, less than 1 mm in width, glabrous in texture.

Ray florets (capitulate):

*Number.*—Average of 65.

*Arrangement.*—Double whorl.

*Shape.*—Spatulate.

*Aspect.*—From horizontal to upright at an angle of 45°.

*Size.*—Average of 2.74 cm in length and 4.6 mm width.

*Petal apex.*—Acute.
*Petal base.*—Cuneate.
*Petal margins.*—Entire.
*Petal texture.*—Glabrous on upper and lower surface.
*Petal color.*—Opening; Upper surface 70B, lower surface 75A with inner stripe of 70B, fully open; upper and lower surface 76C with markings of 76A, fading; upper and lower surface 76B with markings of 76A.

Disk florets (perfect):
*Quantity.*—Average of 93.
*Shape.*—Tubular.
*Size.*—About 6 mm in length and mm in width.
*Color.*—Immature 148C, mature 145C.

Reproductive organs:
*Presence.*—Disk flowers are perfect, ray flowers are carpellate.
*Gynoecium.*—1 Pistil per disk and ray floret, style color 11D.
*Androcoecium.*—1 stamen per disk floret, fused into tube surrounding style, anther color 16A, pollen abundance is moderate and 13A in color.
*Fruit and seed.*—About 158 ovules per floret. Fruit is an achene with a single seed attached to the ovary wall. Seed lacks pappus, have a compressed oval shape with pointed ends, are about 2 to 5 mm in length and 1 to 2 mm in width with a ridged texture and 200D in color.

I claim:

1. A new and distinct cultivar of *Chrysanthemum* plant named '01-127-1' as herein illustrated and described.

* * * * *